United States Patent [19]
Carrico et al.

[11] Patent Number: 5,856,410
[45] Date of Patent: Jan. 5, 1999

[54] POLYACRYLATE SUPERABSORBENT POST-POLYMERIZATION NEUTRALIZED WITH SOLID, NON-HYDROXYL NEUTRALIZING AGENT.

[75] Inventors: Peter W. Carrico, Elgin; Bala V. Nathan, Wheaton, both of Ill.

[73] Assignee: Amcol International Corporation, Arlington Heights, Ill.

[21] Appl. No.: 911,942

[22] Filed: Aug. 20, 1997

Related U.S. Application Data

[63] Continuation of Ser. No. 862,188, May 23, 1997, abandoned.

[51] Int. Cl.$^6$ ............................................. C08F 8/42
[52] U.S. Cl. .................. 525/362; 525/329.9; 525/330.2; 525/367; 525/378
[58] Field of Search ............................. 525/329.9, 330.2, 525/362, 367, 378

[56] References Cited

U.S. PATENT DOCUMENTS

| | | | |
|---|---|---|---|
| 4,062,817 | 12/1977 | Westerman | 260/17.45 G |
| 4,076,663 | 2/1978 | Masuda et al. | 260/17.4 |
| 4,340,706 | 7/1982 | Obayashi et al. | 526/207 |
| 4,506,062 | 3/1985 | Flesher et al. | 526/211 |
| 4,654,039 | 3/1987 | Brandt et al. | 605/368 |
| 4,985,514 | 1/1991 | Kimura et al. | 525/330.2 |
| 4,990,574 | 2/1991 | Yamada | 525/371 |
| 5,002,986 | 3/1991 | Fujiura et al. | 524/47 |
| 5,122,544 | 6/1992 | Bailey et al. | 521/40 |
| 5,314,420 | 5/1994 | Smith et al. | 604/358 |
| 5,385,983 | 1/1995 | Graham | 525/330.2 |

FOREIGN PATENT DOCUMENTS

| | | |
|---|---|---|
| 0 295 438 | 12/1988 | European Pat. Off. . |
| 0 404 184 | 12/1990 | European Pat. Off. . |
| 0 702 031 | 3/1996 | European Pat. Off. . |
| WO 94/09043 | 4/1994 | WIPO . |

*Primary Examiner*—Bernard Lipman
*Attorney, Agent, or Firm*—Marshall, O'Toole, Gerstein, Murray & Borun

[57] ABSTRACT

A new and improved method of manufacturing an acrylic acid superabsorbent polymer, that is manufactured by any known technique, except that the acrylic acid monomer is polymerized to substantial completion before neutralization, and neutralization is accomplished by admixing a solid, e.g., powdered or granular, neutralizing agent into the acrylic acid polymer. Preferably, the neutralizing agent is a solid, non-hydroxide neutralizing agent, such as sodium carbonate, potassium carbonate, ammonium carbonate or mixtures thereof. Cross-linking may be accomplished during polymerization, simultaneously with neutralization, or cross-linking may be carried out in a separate processing step subsequent to neutralization, or both.

28 Claims, No Drawings

POLYACRYLATE SUPERABSORBENT POST-POLYMERIZATION NEUTRALIZED WITH SOLID, NON-HYDROXYL NEUTRALIZING AGENT.

CROSS-REFERENCE TO RELATED APPLICATION

This application is a continuation of application Ser. No. 08/862,188 filed May 23, 1997, now abandoned.

FIELD OF THE INVENTION

The present invention is directed to a method of manufacturing cross-linked acrylic acid superabsorbent polymers and copolymers, useful as absorbents in absorbent structures and absorbent articles, such as diapers, sanitary napkins and the like. More particularly, the present invention is directed to a new and improved method of manufacturing superabsorbent, water-insoluble acrylic polymers by polymerizing an unneutralized acrylic acid (free acrylic acid) monomer to form a polyacrylic acid gel. The polyacrylic acid gel, after polymerization is substantially complete, as evidenced by a substantially reduced rate of temperature rise in the polymerizing acrylic acid monomer solution, then is neutralized by intimately mixing a solid, e.g., powdered neutralizing agent, preferably a solid non-hydroxide neutralizing agent, such as powdered sodium carbonate, powdered potassium carbonate, and/or powdered ammonium carbonate, into the gel, such as by extruding the gel and solid neutralizing agent together. The polymer can be cross-linked sufficiently for water-insolubility during polymerization, simultaneously with the neutralization step and/or in a post-neutralization cross-linking step.

BACKGROUND OF THE INVENTION AND PRIOR ART

Water-insoluble acrylic acid superabsorbent polymers have been in use in absorbent articles, such as diapers, for many years. Such superabsorbent polymers are capable of absorbing many times their weight of water and body fluids and can retain such absorbed liquids under moderate pressure, as measured by absorption under load (AUL). These superabsorbent acrylic polymers have been manufactured by a number of polymerization techniques, including aqueous solution polymerization or bulk polymerization, which maintains an aqueous reaction mixture (or monomer solution) as a single phase until solid particles of polymer are formed. Other techniques for manufacturing superabsorbent acrylic polymer absorbents include, for example, multiphase polymerization processing techniques, such as inverse emulsion polymerization or inverse suspension polymerization. In these multi-phase techniques, the aqueous acrylic monomer solution is suspended in the form of tiny droplets in a matrix of a water-immiscible, inert organic solvent, such as cyclohexane.

In any of the methods for manufacturing water-insoluble polyacrylic superabsorbent polymers, the polyacrylic acid polymer preferably is neutralized at least about 25 mole percent, more preferably at least about 50 mole percent, and usually about 70–75 mole percent for optimum absorbency. Neutralization may be carried out by neutralizing the acrylic acid monomer before polymerization of the monomer, or the polymer may be neutralized after the polymerization reaction is substantially complete. Examples of post polymerization neutralization are disclosed in U.S. Pat. Nos. 4,062,817 and 4,654,039. After polymerization and internal cross-linking of the monomer, followed by partial neutralization, e.g., 50–100 mole percent neutralization, preferably 70–75 mole percent neutralization, the polymer then is subdivided, e.g., shredded, for more efficient drying, then dried and milled to a desired particle size. The polymer preferably then is surface cross-linked and again dried to form the final product.

In accordance with the manufacturing method of the present invention, it has been found that in using any acrylic acid polymerization technique, as briefly described above, for manufacturing acrylic acid-based, water-insoluble superabsorbent polymers, a substantial number of processing improvements can be realized by post-polymerization neutralization using a solid (e.g., powdered or granular) neutralizing agent that is intimately and homogeneously mixed into the polymer gel after substantial completion of the acrylic acid monomer polymerization reaction. Substantial completion of the acrylic acid monomer polymerization reaction is defined herein to be achieved when the rate of increase in temperature of the polymerizing acrylic acid monomer solution, during the polymerization reaction, decreases to about 5° C. per minute or less, preferably to 2° C. per minute or less, and more preferably to about 1° C. per minute or less.

SUMMARY OF THE INVENTION

In brief, the present invention is directed to a new and improved method of manufacturing an acrylic acid superabsorbent polymer, that is manufactured by any known technique, except that the acrylic acid monomer is polymerized to substantial completion before neutralization, and neutralization is accomplished by admixing a solid, e.g., powdered or granular, neutralizing agent into the acrylic acid polymer. Preferably, the neutralizing agent is a solid, non-hydroxide neutralizing agent, such as sodium carbonate, potassium carbonate, ammonium carbonate, bicarbonates of the foregoing, or mixtures thereof. Cross-linking may be accomplished during polymerization, simultaneously with neutralization, or cross-linking may be carried out in a separate processing step subsequent to neutralization, or both.

Accordingly, one aspect of the present invention is to provide a new and improved method of manufacturing a water-insoluble acrylic acid superabsorbent polymer, that includes the steps of polymerizing unneutralized acrylic acid to form a cross-linked acrylic acid polymer gel, and then partially neutralizing the acrylic acid polymer gel by intimately mixing into the gel a neutralizing agent in solid form. Alternatively, internal cross-linking can be achieved after polymerization, as well known in the art.

Suitable mixing apparatus includes, for example, a preliminary mixing apparatus having a relatively wide material-receiving mouth, for receipt of wide ribbons or slabs of polyacrylate gel without requiring a preliminary cutting or chopping station, such as a JAYGO Model AME 60 extruder, preferably followed by a final, more intensive mixer, such as a BEPEX Extrudomix Model EM-6.

Another aspect of the present invention is to provide a method of manufacturing, by post-polymerization neutralization with a solid neutralizing agent, thereby substantially lessening the unit processing time for manufacture and/or equipment capitalization costs (more equipment or more sophisticated equipment is needed to manage exothermic neutralizations with NaOH—whether the neutralization occurs before or after acrylic acid polymerization) and/or operational costs—the running of more sophisticated equipment to remove/control exotherm.

Still another aspect of the present invention is to provide a new and improved method of manufacturing a water-insoluble superabsorbent acrylic acid polymer, capable of up to 100 mole percent neutralization when neutralized after substantial completion of the polymerization reaction using a solid, non-hydroxyl neutralizing agent, without increasing the percentage of extractable acrylic acid or residual (non-polymer) acrylic acid, while maintaining excellent absorbency.

The above and other aspects and advantages of the present invention will become more apparent from the following detailed description of the preferred embodiments.

DETAILED DESCRIPTION OF THE PREFERRED EMBODIMENTS

The present invention is directed to a process for preparing water-insoluble, cross-linked, at least partially neutralized, polyacrylate superabsorbent polymers. The process includes the steps of preparing a monomer solution (reaction mixture) containing an acrylic acid monomer, optionally a cross-linking agent, and a free radical initiator, in an aqueous medium; subjecting this reaction mixture to polymerization conditions to produce a substantially water-insoluble, acrylic acid polymer; and after polymerization is substantially complete, as evidenced by a levelling off of the exothermic heat of reaction (polymerization), neutralizing at least a portion of the acid groups of the acrylic acid polymer with a solid neutralizing agent, preferably a non-hydroxyl neutralizing agent, such as an alkali metal carbonate or bicarbonate, to provide a partially or fully neutralized acrylic acid polymer having a degree of neutralization of at least about 25 mole percent, preferably at least about 70 mole percent, up to 100 mole percent.

In accordance with the manufacturing process of the present invention, cross-linking of the acrylic acid polymer can be accomplished before, during or after acrylic acid polymerization is substantially complete (before neutralization, simultaneously with neutralization, or subsequent to neutralization, in a separate process step). The cross-linking agent serves to render the acrylate polymer of this invention substantially water-insoluble. Suitable cross-linking agents include, for example, (1) compounds having at least two polymerizable double bonds; (2) compounds having at least one polymerizable double bond and at least one functional group reactive with the acrylic acid; (3) compounds having at least two functional groups reactive with the acrylic acid monomer; and (4) polyvalent metal compounds which can form ionic cross-linkages with acrylic acid.

Cross-linking agents having at least two polymerizable double bonds include (1) di- or polyvinyl compounds such as divinylbenzene and divinyltoluene; (2) di-or poly-esters of unsaturated mono- or poly-carboxylic acids with polyols including, for example, di- or triacrylic acid esters of polyols such as ethylene glycol, trimethylol propane triacrylate, glycerine, or polyoxyethylene glycols; (3) bisacrylamides such as N,N-methylenebisacrylamide; (4) carbamyl esters that can be obtained by reacting polyisocyanates with hydroxyl group-containing monomers; (5) di- or poly-allyl ethers of polyols; (6) di- or poly-allyl esters of polycarboxylic acids such as diallyl phthalate, diallyl adipate, and the like; (7) esters of unsaturated mono- or poly-carboxylic acids with mono-allyl esters of polyols such as acrylic acid ester of polyethylene glycol monoallyl ether; and (8) di- or triallyl amine.

Cross-linking agents having at least one polymerizable double bond and at least one functional group reactive with the acrylic acid monomer include N-methylol acrylamide, glycidyl acrylate, and the like. Suitable cross-linking agents having at least two functional groups reactive with the acid-containing monomer material include glyoxal; polyols such as ethylene glycol; polyamines such as alkylene diamines (e.g., ethylene diamine), polyalkylene polyamines, polyepoxides, di- or polyglycidyl ethers, and the like. Suitable polyvalent metal cross-linking agents which can form ionic cross-linkages include oxides, hydroxides and weak acid salts (e.g., carbonate, acetate and the like) of alkaline earth metals (e.g., calcium, magnesium) and zinc, including, for example, calcium oxide and zinc diacetate.

Cross-linking agents of many of the foregoing types are described in greater detail in U.S. Pat. Nos. 4,076,663 and 4,654,039, hereby incorporated by reference. Of all of these cross-linking agents, the most preferred for use herein are the di- or polyesters of unsaturated mono- or polycarboxylic acids with polyols, the bisacrylamides and the di- or triallyl amines. Especially preferred cross-linking agents are N-N'-methylenebisacrylamide, trimethylol propane triacrylate and triallyl amine. The cross-linking agent will generally comprise from about 0.001 mole percent to 5 mole percent of the resulting acrylate superabsorbent polymer.

At least 25 mole percent of these acid groups of the acrylic acid must be neutralized to form the partially or fully neutralized acrylate polymer of the present invention. Preferably at least 50 mole percent, more preferably 70–80 mole percent, up to 100 mole percent, of the acrylic acid monomers are neutralized with a solid, non-hydroxyl neutralizing agent, preferably powdered potassium carbonate, ammonium carbonate and/or sodium carbonate.

By polymerizing the acrylic acid monomer prior to neutralization, and then neutralizing with a solid non-hydroxyl neutralizing agent, a substantial number of processing improvements are realized, as described in more detail hereinafter.

One component of the aqueous reaction mixture used to prepare the acrylate polymers comprises a free radical initiator. Such an initiator may be any conventional water-soluble polymerization initiator including, for example, peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems also can be utilized. Such systems are formed by combining the foregoing peroxygen compounds with reducing agents such as sodium bisulfite, L-ascorbic acid or ferrous salts. If utilized, the initiator material can comprise up to about 5 mole percent based on the total moles of acrylic acid monomer present. More preferably the initiator comprises from about 0.001 to 0.5 mole percent based on the total moles of acrylic acid monomer in the monomer solution.

Polymerization of the acrylic acid in the monomer solution is accomplished at a preferred polymerization temperature of from about −10° C. to 100° C., more preferably from about 50° C. to 80° C., utilizing a preferred, low initiation temperature of about −10° C. to about 20° C., preferably −10° C. to 10° C. Temperatures within the preferred range are generally somewhat lower than most which have been conventionally utilized to prepare hydrogel-forming materials of this same general type. Use of such lower temperatures promotes the preparation of acrylates of higher molecular weight, higher absorbency, relatively low levels of extractable polymers, and provides a process of higher yield.

Polymerization can also include subjecting the monomer solution (reaction mixture), or portions thereof, to any conventional form of polymerization activating irradiation provided the monomer contains one or more UV-activatable initiators. Use of radioactive, electronic, ultraviolet or other electromagnetic radiation is a conventional polymerization technique and can be employed in the manufacturing process of the present invention.

Neutralization of at least 25 mole percent of the acid groups on the acrylic acid polymer, preferably 70–80 mole percent, and up to 100 mole percent, is accomplished after polymerization of the acrylic acid monomers is substantially complete. Since polymerization of the acrylic acid in the monomer solution, in accordance with the present invention, must take place using acrylic acid monomers in their free acid form, neutralization should be carried out after the polymerization reaction is substantially complete.

An additional optional process step includes drying and recovery of the acrylate polymer product. The acrylate polymer formed in the reaction mixture can be dried after neutralization and cross-linking by any conventional method. It appears that polymer manufactured in accordance with the present invention (post polymerization neutralization) is easier to dry. For example, the gel, after neutralization and cross-linking, can be directly dried by subjecting the acrylate polymer to temperatures of from about 40° C. to 220° C., preferably from about 40° C. to about 150° C., for a period of time sufficient to form a semi-solid mass of material.

Alternatively, water can be removed from the reaction mixture by azeotropic distillation. In such a procedure an azeotrope-forming solvent, such as cyclohexane, is combined with the gelled mass of polymer, and the temperature of the resulting mixture is maintained at or above the boiling point of the resulting azeotrope. In yet another drying procedure, the gelled polymer can be treated with a dewatering solvent, such as methanol. Combinations of these drying procedures may also be utilized.

The dewatered mass of polymer can be chopped or pulverized to form particles of the dried superabsorbent acrylate polymer useful as absorbents in absorbent structures and articles.

Preferably, the acrylate polymer manufacturing process of this invention will be carried out using an aqueous solution polymerization process. In such a solution polymerization process, water-miscible solvents and/or other compatible optional ingredients such as surfactants can be added to the aqueous reaction mixture. In such procedures, the aqueous reaction mixture will be generally maintained as a single-phase system until solid particles of polymer are formed.

It is also possible, however, to carry out the polymerization process using multi-phase polymerization processing techniques, such as inverse emulsion polymerization or inverse suspension polymerization processes. In the inverse emulsion polymerization or inverse suspension polymerization processes, the aqueous reaction mixture, as hereinbefore described, is suspended in the form of tiny droplets in a matrix of a water-immiscible, inert organic solvent, such as cyclohexane. Polymerization in such processes still occurs in the aqueous phase, but suspensions or emulsions of this aqueous phase in an organic solvent permits better control of the exothermic heat of polymerization and further provides the flexibility of adding one or more of the aqueous reaction mixture components in a controlled manner to the organic phase.

Inverse suspension polymerization processes are described in greater detail in Obayashi, et al., U.S. Pat. No. 4,340,706; and in Flesher, et al. U.S. Pat. No. 4,506,062, hereby incorporated by reference. As noted in those patents, when inverse suspension polymerization or inverse emulsion polymerization techniques are employed, additional ingredients such as surfactants, emulsifiers, polymerization stabilizers and the like may be added to the acrylic acid reaction mixture. When inverse phase processes, or any other process employing organic solvent are utilized, it is important that the polymer recovered from such processes be treated to remove substantially all of the excess organic solvent. It is highly preferred, for example, that the acrylate polymers manufactured in accordance with the present invention contain no more than about 0.5% by weight of residual organic solvent.

It should also be noted that the composition of the aqueous reaction mixture described herein applies to the overall polymerization reaction mixture if a substantially single-phase aqueous solution polymerization is utilized, but applies only to the aqueous phase of the overall reaction mixture if two-phase inverse suspension or inverse emulsion polymerization techniques are employed. Thus, for purposes of the present invention, the term "monomer solution", or "aqueous reaction mixture" also means and applies to the aqueous phase of a two-phase overall or total reaction mixture of inverse suspension or inverse emulsion processes.

The dried and neutralized acrylate polymers are employed in a conventional manner, preferably in combination with hydrophilic fiber material to form improved absorbent structures useful in absorbent articles. Frequently, such absorbent structures will comprise combinations of hydrophilic fiber material and discrete particles of the acrylate polymer manufactured in accordance with the present invention.

Various types of hydrophilic fiber material can be used in the absorbent structures containing the acrylate superabsorbent polymers of the present invention. Any type of hydrophilic fiber which is suitable for use in conventional absorbent products is also suitable for use in the absorbent structures herein. Specific examples of such fibers include cellulose fibers, rayon, and polyester fibers. Other examples of suitable hydrophilic fibers are hydrophilized hydrophobic fibers, such as surfactant-treated or silica-treated thermoplastic fibers. For reasons of availability and cost, cellulose fibers, in particular wood pulp fibers, are preferred. The absorbent structures will generally comprise from about 0% to about 98% by weight, and more preferably from about 65% to about 90% by weight of hydrophilic fiber material.

EXAMPLE 1

Polyacrylic acid for superabsorbent use can be made from a solution of acrylic acid in water in the concentration range of about 10% to about 40% by weight, preferably about 15% to about 35% by weight acrylic acid, more preferably about 20% to about 30% by weight, and most preferably about 25% to about 28% by weight, with appropriate amounts of internal cross-links. Polymer so obtained was neutralized to 60–95 mole percent (the post-neutralization "PN" process) with any of sodium carbonate, potassium carbonate, ammonium carbonate, or mixtures.

In experiments with a starting solution containing 25% by weight acrylic acid, 0.07 mole percent of internal cross-linker methylene bisacrylamide (a); appropriate levels of initiators (b), (2,2'-azobis(2-amidinopropane) dihydrochloride); and sodium persulfate (c), and initiator temperature of 18° C., yielded a polymer which when neutralized with sodium carbonate powder to 75 mole percent and then dried, milled, sized and post modified by surface cross-linking yielded a product with an average gel volume of 41.2 gm/gm; an absorption under load (AUL) of (1) 0.28 psi load=34.1 gm/gm. (2) 0.7 psi load=27.1 gm/gm; a weight percent extractables of 7.7%; and a residual acrylic acid content of 140 parts per million.

EXAMPLE 2

In a test, superabsorbent polymer obtained from conventional methods, namely using preneutralized acrylic acid, was compared against polymer obtained by process described in Example 1.

Thus, the test involved making preneutralized polymer starting with a solution of acrylic acid in water in the concentration range 15–35% by weight, more preferably 20–30% by weight, and most preferably 25–30% by weight, neutralizing 75–80 mole percent of the acid in the solution with sodium carbonate, mixing with appropriate concentrations of internal cross-links, and polymerizing the resultant mixture. Product so obtained was post modified by surface cross-linking in the same way as in Example 1.

In experiments starting with a monomer solution containing a combination of acrylic acid and sodium acrylate in the mole ratio of 25/75 and at a concentration of 28.5% by weight in water using methylene bisacrylamide internal cross-linker (a) at the same concentration as in Example 1 and at an initial (initiation) temperature of 18° C. yielded a polymer which when dried, milled and sized and post modified by surface cross-linking as in Example 1, yielded a product with the following properties:

|  | Gel Volume gm/gm | 0.28 psi AUL gm/gm | 0.7 psi AUL gm/gm | Extractables wt. % |
|---|---|---|---|---|
| Avg. | 38.7 | 31.1 | 24.1 | 11.2 |
| Std. Dev. | 1.32 | 0.86 | 1.17 | 4.46 |

EXAMPLE 3

Polymer made as in Example 1 at lower initiation temperatures yielded better quality product than at higher initiation temperatures. In a test to study the effect of the initiation temperature, the acrylic acid solution as in Example 1 was progressively cooled to 10° C. before initiating the polymerization and compared with product obtained by initiating at 18° C.

Experiments repeated as in Example 1 but at an initial monomer temperature of 10° C. yielded the following results:

| Gel Vol. gm/gm | 0.28 psi AUL gm/gm | 0.7 psi AUL gm/gm | Extractables wt. % | Residual Acrylic Acid (ppm) |
|---|---|---|---|---|
| 43.9 | 36.4 | 27.7 | 5.6 | 153 |
| 41.9 | 35.1 | 29.0 | 6.5 | 123 |
| 40.6 | 35.1 | 27.8 | 6.6 | 176 |
| 38.5 | 34.7 | 29.1 | 4.5 | 95 |
| 43.0 | 35.1 | 26.7 | 7.1 | 173 |
| 38.4 | 33.0 | 28.1 | 7.1 | 113 |
| 42.0 | 33.1 | 28.0 | 7.5 | 122 |
| 39.8 | 34.3 | 27.6 | 4.6 | 165 |
| 41.1 | 35.1 | 27.9 | 4.2 | 103 |
|  |  | AVERAGES |  |  |
| 41.0 | 34.6 | 28.0 | 6.0 | 135 |

EXAMPLE 4

Polymer made as in Example 1 was successfully neutralized to 60–95 mole percent, and more preferably to 75–80 mole percent in continuous processing machines such as "Z blade" mixer/extruders, "Sigma blade" mixer/extruders, "pug mills", and "meat grinders" without any noticeable differences in product quality.

Neutralization of polymer was accomplished using dry powdery bases such as sodium carbonate, potassium carbonate and ammonium carbonate. The neutralized polymer so obtained was homogeneous, porous and easier to dry. The dry polymer was of comparable/better quality than product made from preneutralization processes.

Unreacted monomer acids and their salts were successfully scavenged by adding sodium metabisulfite as a monomer scavenger at 0.25% by weight, based on the weight of polymer, in further processing of the neutralized polymer in continuous processing mixer/kneader/extruder machines such as those with interrupted flights, intermediate die plates, meat grinders, extruders, and "Z blade" mixer extruders. Monomer scavengers, such as sodium metabisulfite can be added in amounts in the range of about 0.01% to about 5% by weight based on the dry weight of the polymer, preferably about 0.02% to about 2% by weight, more preferably about 0.02% to about 0.5% by weight.

EXAMPLE 5

The neutralization and monomer scavenging as in Example 5 were also equally successfully done in a single machine with multi-functional capabilities. A Winkworth "Z-blade" mixer/extruder was modified to have an extended extruder shaft with part full flights and part interrupted flights and with intermediate die plates for this purpose.

Generally, in all studies, a single machine, appropriately modified as outlined, produces products with comparable performance characteristics as multiple machines and in each case the performance is comparable or superior to conventional pre-neutralized polymer.

EXAMPLE 6

Neutralization of polymeric acrylic acid was accomplished in one machine. Machines such as a "Z" blade mixer/extruder, pug mill, or a meat grinder were employed for this purpose.

EXAMPLE 7

Neutralization and monomer scavenging were done successively in separate steps and compared with results from Example 6. Product obtained by separating the process steps was of superior quality than that obtained in Example 5.

EXAMPLE 8

Comparison of percent extractables from the PN process with that of the conventional process showed that the PN process produced significantly less extractables (compare data for Example 2 to Examples 1 and 3).

EXAMPLE 9

The percentage conversion of monomer to polymer was found to be significantly higher for the PN process, making the monomer scavenging operation easier in subsequent processing.

For example, typical monomer conversions to polymer in the PN process ranged from 98.5% to 99.7% and occasionally as high as 99.9% (see table below), where as for preneutralized monomers the conversion to polymer were typically 90–95% and occasionally as high as 97%.

Monomer Conversion For PN Process

| Trial | Conversion |
| --- | --- |
| Trial 1 | 99.70% |
| Trial 2 | 99.58% |
| Trial 3 | 99.22% |

What is claimed is:

1. A method of manufacturing a polymer of acrylic acid comprising polymerizing an aqueous solution of unneutralized acrylic acid and, after polymerization is substantially complete and the unneutralized acrylic acid forms an unneutralized poly-acrylic acid gel, homogeneously and intimately mixing a solid, non-hydroxyl neutralizing agent into the gel in an amount sufficient to neutralize at least 25 mole percent of the acid moieties of said polyacrylic acid, and cross-linking said polyacrylic acid gel in an amount sufficient to make said polymer water-insoluble.

2. The method of claim 1, wherein the aqueous solution of acrylic acid has an acrylic acid concentration of about 10% to about 40% by weight.

3. The method of claim 1, wherein the aqueous solution of acrylic acid has an acrylic acid concentration of about 15% to about 35% by weight.

4. The method of claim 1, wherein the neutralizing agent has a strength such that a 1% aqueous solution of said neutralizing agent, at 25° C., has a pH in the range of 9 to 11.

5. The method of claim 1, wherein the neutralizing agent is selected from the group consisting of sodium carbonate, potassium carbonate, ammonium carbonate, and combinations thereof.

6. The method of claim 5, wherein the neutralizing agent is mixed into the polyacrylic acid gel in an amount sufficient to neutralize at least about 50 mole percent of the acid moieties of said polyacrylic acid.

7. The method of claim 6, wherein the neutralizing agent is mixed into the polyacrylic acid gel in an amount sufficient to neutralize about 70–80 mole percent of said acid moieties of said polyacrylic acid.

8. The method of claim 7, wherein the neutralizing agent is mixed into the polyacrylic acid gel in an amount sufficient to neutralize about 70–95 mole percent of said acid moieties of said polyacrylic acid.

9. The method of claim 6, wherein the neutralizing agent is mixed into the polyacrylic acid gel in an amount sufficient to neutralize about 90–100 mole percent of said acid moieties of said polyacrylic acid.

10. The method of claim 1, wherein polymerization of the aqueous solution of acrylic acid is initiated at an acrylic acid solution temperature in the range of −10° C. to about 20° C.

11. The method of claim 10, wherein polymerization of the aqueous solution of acrylic acid is initiated at an acrylic acid solution temperature in the range of −10° C. to about 10° C.

12. The method of claim 11, wherein polymerization of the aqueous solution of acrylic acid is initiated at an acrylic acid solution temperature in the range of −10° C. to about 5° C.

13. The method of claim 12, wherein polymerization of the aqueous solution of acrylic acid is initiated at an acrylic acid solution temperature in the range of −10° C. to about 0° C.

14. The method of claim 1, further including the step of adding an acrylic acid monomer scavenger to the polyacrylic acid gel.

15. The method of claim 14, wherein the acrylic acid monomer scavenger is added to the polyacrylic acid gel prior to adding the solid neutralizing agent to the polyacrylic acid gel.

16. The method of claim 14, wherein the acrylic acid monomer scavenger is added to the polyacrylic acid gel after adding the solid neutralizing agent to the polyacrylic acid gel.

17. The method of claim 15, wherein the acrylic acid monomer scavenger comprises an alkali metal metabisulfite.

18. The method of claim 17, wherein the alkali metal metabisulfite is sodium metabisulfite.

19. The method of claim 1, wherein the aqueous solution of acrylic acid includes an acrylic acid polymerization initiator in an amount of about 0.001 to about 5 mole percent, based on the total moles of acrylic acid monomer in the aqueous solution of acrylic acid.

20. The method of claim 19, wherein the concentration of polymerization initiator in the aqueous solution of acrylic acid is about 0.001 to about 0.5 mole percent, based on the total moles of acrylic acid monomer in the aqueous solution of acrylic acid.

21. The method of claim 1, further including the step of drying the neutralized, cross-linked polymer at a temperature in the range of about 40° C. to about 220° C.

22. The method of claim 1, wherein the polymer is cross-linked prior to neutralization.

23. The method of claim 1, wherein the polymer is cross-linked after neutralization.

24. The method of claim 1, wherein intimate mixing of the solid neutralizing agent into the gel is accomplished in a mixing and extruding apparatus.

25. The method of claim 24, wherein the mixing and extruding apparatus includes a multiple die plate configuration.

26. The method of claim 25, wherein a discharge opening for extrusion of polyacrylate gel therethrough includes an opening defined by a discharge tube having an end flared outwardly.

27. The method of claim 1, including intimately mixing the solid neutralizing agent into the gel in a single mixing apparatus.

28. The method of claim 1, including intimately mixing a portion of the solid neutralizing agent into the gel in a first mixing apparatus to form a partially mixed gel, and then mixing additional solid neutralizing agent into the partially mixed gel in a second, more intensive mixing apparatus.

* * * * *